United States Patent [19]

Umezawa

[11] 4,101,650
[45] Jul. 18, 1978

[54] PEPSTATIN FLOATING MINICAPSULES

[75] Inventor: Hamao Umezawa, Tokyo, Japan

[73] Assignee: Zaidan Hojin Biseibutsu Kagaku Kenkyu Kai, Tokyo, Japan

[21] Appl. No.: 785,268

[22] Filed: Apr. 6, 1977

[51] Int. Cl.$^2$ .................. A61K 9/46; A61K 9/50; A61K 37/64
[52] U.S. Cl. .................................. 424/44; 424/14
[58] Field of Search .................................. 424/14, 44

[56] References Cited

U.S. PATENT DOCUMENTS

| | | | |
|---|---|---|---|
| 536,155 | 3/1895 | Noyes | 424/44 |
| 2,125,577 | 8/1938 | Matsumae | 424/44 |
| 2,540,253 | 2/1951 | Gakenheimer | 424/44 |
| 3,131,123 | 4/1964 | Masquelier | 424/44 X |
| 3,136,692 | 6/1964 | Bandglin | 424/44 |
| 3,418,999 | 12/1968 | Davis | 424/14 X |
| 3,444,290 | 5/1969 | Wai | 424/14 X |
| 3,740,319 | 6/1973 | Umezawa et al. | 195/80 R |
| 3,887,700 | 6/1975 | Boncey et al. | 424/44 |
| 4,036,228 | 7/1977 | Theeunbs | 424/14 X |

*Primary Examiner*—Shep K. Rose
*Attorney, Agent, or Firm*—Herbert W. Taylor, Jr.

[57] ABSTRACT

Increased duration of inhibition of secretion of pepsin in man by oral administration of pepstatin is achieved by the use of a formulation in which pepstatin is coated on very small granules of sodium bicarbonate to form floating minicapsules.

15 Claims, No Drawings

PEPSTATIN FLOATING MINICAPSULES

BACKGROUND OF THE INVENTION

1. Field of the Invention

This invention relates to specially formulated capsules of pepstatin for use in man by oral administration to inhibit pepsin in the stomach.

2. Description of the Prior Art

Pepstatin is a generic name of a group of compounds which have the following structure (T. Aoyagi and H. Umezawa, Protease and Biological Control, p. 429–454, 1975, Cold Spring Harbor Laboratory): RCO-L-Val-L-Val-AHMHA-L-Ala-AHMHA, where AHMHA is (3S,4S)-4-amino-3-hydroxy-6-methylheptanoic acid. Pepstatin inhibits pepsin and cathepsin D very strongly. It also exhibits a relative strong inhibiton against renin. Among pepstatin group compounds, biological activities have been studied most in detail on that which contains isopentanoyl group as RCO—. This compound has been shown by clinical studies to be useful in treatment of gastric and duodenal ulcers in humans.

Adminstration of ordinary capsules containing pepstatin four to seven times per day has been shown to exhibit a therapeutic effect against gastric and duodenal ulcers. It has never shown any toxic signs. In this procedure an amount of pepstatin sufficient to suppress pepsin stayed for one hour in the stomach (T. Aoyagi, S. Kunimoto, H. Morishima, T. Takeuchi and H. Umezawa, Journal of Antibiotics 24, 687–694, 1971). For additional information on pepstatin see U.S. Pat. Nos. 3,740,319; 3,869,347; 3,063,579; 3,975,366 and J. Antibiotics 23, 259–262 and 263–265 (1970).

Although administration of pepstatin placed in ordinary capsules showed the desired effect, it was hoped to develop a new preparation which would permit pepstatin to stay longer in the stomach.

SUMMARY OF THE INVENTION

This invention is related to the formulation of pepstatin in a long-acting minicapsule and to its use for the treatment of gastric and duodenal ulcers. This mini capsule in which carbon dioxide gas is produced by gastric acid floats, stays in the stomach and releases pepstatin continuously. It has been shown that in the case when these minicapsules are given immediately after a meal, this capsule stays for 3–5 hours in the stomach and releases enough pepstatin to suppress the pepsin activity.

There is further provided by the present invention a composition in oral dosage form comprising mini capsules having a diameter in the range of 0.1 to 2 mm. in which the center comprises a granule of sodium bicarbonate admixed if desired with at least one conventional solubilizing diluent such as a sugar, preferably lactose, and/or at least one water-soluble and solvent-soluble binder such as polyvinylpyrrolidone, said granule being coated with a conventional water-soluble, film-coating agent such as hydroxypropylmethylcellulose and said center being coated with pepstatin, said sodium bicarbonate being present in a weight in the range of two to ten, and preferbly about five, times the weight of said pepstatin and said minicapsule being further coated on the outside with a conventional water-soluble film-coating agent such as hydroxypropylmethylcellulose.

There is also provided by the present invention the process for reducing the secretion of pepsin by the human stomach which comprises the oral administration in a patient being treated for a gastric or duodenal ulcer of an amount effective to cause said reduction, and preferably the administration four or five times a day in a dose of 50 to 200 mgm. pepstatin per dose, of a composition in oral dosage form comprising minicapsules having a diameter in the range of 0.1 to 2 mm. in which the center comprises a granule of sodium bicarbonate admixed if desired with at least one conventional solubilizing diluent such as a sugar, preferably lactose, and/or at least one water-soluble and solvent-soluble binder such as polyvinylpyrrolidone, said granule being coated with a conventional water-soluble, film-coating agent such as hydroxypropylmethylcellulose and said center being coated with pepstatin, said sodium bicarbonate being present in a weight in the range of two to 10, and preferably about five, times the weight of said pepstatin and said minicapsule being further coated on the outside with a conventional water-soluble, film-coating agent such as hydroxypropylmethylcellulose.

In this invention, fine granules of sodium bicarbonate are coated with a conventional coating agent and this coated powder of sodium bicarbonate is mixed with pepstatin and a diluting agent or a binder if necessary, or all of these components are mixed and coated by conventional coating agents and the minicapsules are thus prepared.

By this invention, any size of minicapsules can be prepared, that is, minicapsules from 1/10 to several mm. in diameter can be prepared. For the encapsulation, all known conventional methods such as spray-coating methods, spray-drying methods and dipping methods can be applied.

The minicapsules thus prepared can be given to patients as such or after being placed in ordinary hard capsules.

As already described, pepstatin-minicapsules prepared by this invention release enough pepstatin to suppress pepsin for 3 to 5 hours.

DESCRIPTION OF THE PREFERRED EMBODIMENTS

EXAMPLE 1

Fine granules of 943.4 g. of sodium bicarbonate, 37.7 g. of lactose and 18.9 g. of povidone (polyvinylpyrrolidone) were placed in a coating pan (the diameter was 60 cm.) and spray-coated with 2% methanol solution of hydroxypropylmethylcellulose by the use of Airless-Spray. This coating procedure was repeated several times. The granules thus coated were screened by 100–150 mesh screen to remove the finer coagulated powders of the coating agents which passed through the screen.

Finely powdered pepstatin of 180 g. was mixed with 10 liters of 2% solution of hydroxypolypropylmethylcellulose in methanol and this pepstatin suspension was sprayed on the granules described above. In this case, the spraying procedure was repeated until all of the pepstatin-hydroxypropylmethylcellulose mixture solution was used up. Thereafter, the minicapsules thus prepared were dried under reduced pressure at room temperature.

When the minicapsules were added to artificial human gastric juice the time to release 50% of the pepstatin was 2.5 hours.

EXAMPLE 2

Fine granules of 943.4 g. of sodium bicarbonate, 37.7 g. of lactose and 18.9 g of povidone were mixed and this mixture (1.0 kg.) was mixed with fine granules of 200 g of pepstatin. This mixture was placed in a coating pan and coated with 2% methanol solution of hydroxypropylmethylcellulose by Airless-Spray. This coating procedure was repeated several times. The coated granules were screened by 100–150 mesh screen to remove the coagulated coating agents which passed through the screen. Thereafter, the pepstatin minicapsules were dried under reduced pressure.

When these minicapsules were added to an artificial human gastric juice, the time taken to release 50% of the pepstatin was 3 hours.

Examples of Administration of Pepstatin Floating Minicapsules

The minicapsules prepared above are now called pepstatin-floating minicapsules. The minicapsules prepared by the method described in Example 2 contained 10% pepstatin. When 1.0 g. of this minicapsule was given to 2 volunteers immediately after a meal and 3 hours thereafter the gastric juice was taken, the gastric juices showed almost no pepsin activity. The pepsin activity was tested by the method using hemoglobin as the substrate as described in the following paper: T. Aoyagi, S Kunimoto, H. Morishima, T. Takeuchi and H. Umezawa, Journal of Antibiotics 24, 687–694 (1971). When 1.0 g of the pepstatin-floating minicapsule was given to 2 volunteers immediately after a meal and the gastric juice was taken 5 hours thereafter, the pepsin activity was 30–60% of the control gastric juice taken without administration of pepstatin-floating minicapsules.

I claim:

1. A composition in oral dosage form comprising minicapsules having a diameter in the range of 0.1 to 2 mm. in which the center comprises a granule of sodium bicarbonate, said granule being coated with a conventional water-soluble, film-coating agent and said center being coated with pepstatin.

2. A composition in oral dosage form comprising minicapsules having a diameter in the range of 0.1 to 2 mm. in which the center comprises a granule of sodium bicarbonate, said granule being coated with a conventional water-soluble, film-coating agent and said center being coated with pepstatin, said sodium bicarbonate being present in a weight in the range of two to 10 times the weight of said pepstatin.

3. A composition in oral dosage form comprising minicapsules having a diameter in the range of 0.1 to 2 mm. in which the center comprises a granule of sodium bicarbonate, said granule being coated with a conventional water-soluble, film-coating agent and said center being coated with pepstatin, said sodium bicarbonate being present in a weight of about five times the weight of said pepstatin.

4. A composition in oral dosage form comprising minicapsules having a diameter in the range of 0.1 to 2 mm. in which the center comprises a granule of sodium bicarbonate admixed with at least one conventional solubilizing diluent and at least one water-soluble and solvent-soluble binder, said granule being coated with a conventional water-soluble, film-coating agent and said center being coated with pepstatin, said sodium bicarbonate being present in a weight in the range of two to 10 times the weight of said pepstatin.

5. A composition in oral dosage form comprising minicapsules having a diameter in the range of 0.1 to 2 mm. in which the center comprises a granule of sodium bicarbonate admixed with lactose and polyvinylpyrrolidone, said granule being coated with a conventional water-soluble, film-coating agent and said center being coated with pepstatin, said sodium bicarbonate being present in a weight in the range of two to 10 times the weight of said pepstatin.

6. The process for reducing the secretion of pepsin by the human stomach which comprises the oral administration in a patient being treated for a gastric or duodenal ulcer of an amount effective to cause said reduction of a composition in oral dosage form comprising minicapsules having a diameter in the range of 0.1 to 2 mm. in which the center comprises a granule of sodium bicarbonate, said granule being coated with a conventional water-soluble, film-coating agent and said center being coated with pepstatin.

7. The process for reducing the secretion of pepsin by the human stomach which comprises the oral administration in a patient being treated for a gastric or duodenal ulcer of an amount effective to cause said reduction of a composition in oral dosage form comprising minicapsules having a diameter in the range of 0.1 to 2 mm. in which the center comprises a granule of sodium bicarbonate, said granule being coated with a conventional water-soluble, film-coating agent and said center being coated with pepstatin, said sodium bicarbonate being present in a weight in the range of two to 10 times the weight of said pepstatin.

8. The process of reducing the secretion of pepsin by the human stomach which comprises the oral administration in a patient being treated for a gastric or duodenal ulcer of an amount effective to cause said reduction of a composition in oral dosage form comprising minicapsules having a diameter in the range of 0.1 to 2 mm. in which the center comprises a granule of sodium bicarbonate, said granule being coated with a conventional water-soluble, film-coating agent and said center being coated with pepstatin, said sodium bicarbonate being present in a weight of about five times the weight of said pepstatin.

9. The process for reducing the secretion of pepsin by the human stomach which comprises the oral administration in a patient being treated for a gastric or duodenal ulcer of an amount effective to cause said reduction of a composition in oral dosage form comprising minicapsules having a diameter in the rage of 0.1 to 2 mm. in which the center comprises a granule of sodium bicarbonate admixed with at least one conventional solubilizing diluent and at least one water-soluble and solvent-soluble binder, said granule being coated with a conventional water-soluble, film-coating agent and said center being coated with pepstatin, said sodium bicarbonate being present in a weight in the range of two to 10 times the weight of said pepstatin.

10. The process for reducing the secretion of pepsin by the human stomach which comprises the oral administration in a patient being treated for a gastric or duodenal ulcer of an amount effective to cause said reduction of a composition in oral dosage form comprising minicapsules having a diameter in the range of 0.1 to 2 mm. in which the center comprises a granule of sodium bicarbonate admixed with lactose and polyvinylpyrrolidone, said granule being coated with a conventional water-soluble, film-coating agent and said center being coated with pepstatin, said sodium bicarbonate being present in a weight in the range of two to 10 times the weight of said pepstatin.

11. The process for reducing the secretion of pepsin by the human stomach which comprises the oral administration in a patient being treated for a gastric or duodenal ulcer of an amount containing 50 to 200 mgm. pepstatin per dose of a composition in oral dosage form comprising minicapsules having a diameter in the range of 0.1 to 2 mm. in which the center comprises a granule of sodium bicarbonate, said granule being coated with a conventional water-soluble, film-coating agent and said center being coated with pepstatin.

12. The process for reducing the secretion of pepsin by the human stomach which comprises the oral administration in a patient being treated for a gastric or duodenal ulcer of an amount containing 50 to 200 mgm. pepstatin per dose of a composition in oral dosage form comprising minicapsules having a diameter in the range of 0.1 to 2 mm. in which the center comprises a granule of sodium bicarbonate, said granule being coated with a conventional water-soluble, film-coating agent and said center being coated with pepstatin, said sodium bicarbonate being present in a weight in the range of two to 10 times the weight of said pepstatin.

13. The process for reducing the secretion of pepsin by the human stomach which comprises the oral administration in a patient being treated for a gastric or duodenal ulcer of an amount containing 50 to 200 mgm. pepstatin per dose of a composition in oral dosage form comprising minicapsules having a diameter in the range of 0.1 to 2 mm. in which the center comprises a granule of sodium bicarbonate, said granule being coated with a conventional water-soluble, film-coating agent and said center being coated with pepstatin, said sodium bicarbonate being present in a weight of about five times the weight of said pepstatin.

14. The process for reducing the secretion of pepsin by the human stomach which comprises the oral administration in a patient being treated for a gastric or duodenal ulcer of an amount containing 50 to 200 mgm. pepstatin per dose of a composition in oral dosage form comprising minicapsules having a diameter in the range of 0.1 to 2 mm. in which the center comprises a granule of sodium bicarbonate admixed with at least one conventional solubilizing diluent and at least one water-soluble and solvent-soluble binder, said granule being coated with a conventional water-soluble, film-coating agent and said center being coated with pepstatin, said sodium bicarbonate being present in a weight in the range of two to 10 times the weight of said pepstatin.

15. The process for reducing the secretion of pepsin by the human stomach which comprises the oral administration in a patient being treated for a gastric or duodenal ulcer of an amount containing 50 to 200 mgm. pepstatin per dose of a composition in oral dosage form comprising minicapsules having a diameter in the range of 0.1 to 2 mm. in which the center comprises a granule of sodium bicarbonate admixed with lactose and polyvinylpyrrolidone, said granule being coated with a conventional water-soluble, film-coating agent and said center being coated with pepstatin, said sodium bicarbonate being present in a weight in the range of two to 10 times the weight of said pepstatin.

* * * * *